(12) United States Patent
Pastore et al.

(10) Patent No.: US 9,008,746 B2
(45) Date of Patent: Apr. 14, 2015

(54) METHOD AND APPARATUS FOR LOCALIZING MYOCARDIAL INFARCTION DURING CATHETERIZATION

(75) Inventors: Joseph M. Pastore, Concord, OH (US); Steven D. Girouard, Chagrin Falls, OH (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 824 days.

(21) Appl. No.: 12/628,390

(22) Filed: Dec. 1, 2009

(65) Prior Publication Data

US 2010/0081948 A1 Apr. 1, 2010

Related U.S. Application Data

(62) Division of application No. 10/871,865, filed on Jun. 18, 2004, now Pat. No. 7,640,046.

(51) Int. Cl.
| | |
|---|---|
| *A61B 5/04* | (2006.01) |
| *A61B 5/00* | (2006.01) |
| *A61B 5/0265* | (2006.01) |
| *A61B 5/11* | (2006.01) |
| *A61B 8/12* | (2006.01) |
| *A61N 1/37* | (2006.01) |

(52) U.S. Cl.
CPC ............. *A61B 5/4839* (2013.01); *A61B 5/0071* (2013.01); *A61B 5/0084* (2013.01); *A61B 5/0265* (2013.01); *A61B 5/1107* (2013.01); *A61B 8/12* (2013.01); *A61B 2562/0219* (2013.01); *A61N 1/3702* (2013.01); *A61B 5/6869* (2013.01)

(58) Field of Classification Search
USPC ............... 607/374–375; 600/374–375
See application file for complete search history.

(56) References Cited

U.S. PATENT DOCUMENTS

| | | | |
|---|---|---|---|
| 4,867,963 A | | 9/1989 | Maurer et al. |
| 5,106,387 A | | 4/1992 | Kittrell et al. |
| 5,161,531 A | | 11/1992 | Parsons et al. |
| 5,345,941 A | | 9/1994 | Rava et al. |
| 5,417,215 A | | 5/1995 | Evans et al. |
| 5,421,337 A | | 6/1995 | Richards-Kortum et al. |
| 5,447,529 A | | 9/1995 | Marchlinski et al. |
| 5,456,252 A | | 10/1995 | Vari et al. |
| 5,492,119 A | * | 2/1996 | Abrams ................ 600/375 |
| 5,497,770 A | | 3/1996 | Morcos et al. |
| 5,562,721 A | | 10/1996 | Marchlinski et al. |

(Continued)

OTHER PUBLICATIONS

U.S. Appl. No. 10/871,865, Advisory Action mailed Apr. 17, 2008, 3 pgs.

(Continued)

*Primary Examiner* — Brian T Gedeon
(74) *Attorney, Agent, or Firm* — Schwegman Lundberg & Woessner, P.A.

(57) ABSTRACT

A catheter with a tissue property sensor provides for localization of myocardial infarction (MI) by utilizing one or more differences between properties of infarcted myocardial tissue and properties of normal myocardial tissue. The tissue property sensor is to be placed on endocardial wall or epicardial wall during catheterization to sense at least one tissue property allowing for detection of MI. In one embodiment, the tissue property sensor includes a contractility sensor and senses a tissue property in various locations on endocardial wall or epicardial wall and detects substantial changes in the tissue property that indicate a boundary between infarcted tissue and normal tissue.

20 Claims, 8 Drawing Sheets

(56) References Cited

U.S. PATENT DOCUMENTS

| | | | |
|---|---|---|---|
| 5,673,704 | A | 10/1997 | Marchlinski et al. |
| 5,738,096 | A | 4/1998 | Ben-Haim |
| 5,813,403 | A | 9/1998 | Soller et al. |
| 5,865,738 | A | 2/1999 | Morcos et al. |
| 6,021,310 | A | 2/2000 | Thorne |
| 6,021,350 | A | 2/2000 | Mathson |
| 6,024,705 | A | 2/2000 | Schlager et al. |
| 6,055,451 | A | 4/2000 | Bambot et al. |
| 6,077,236 | A * | 6/2000 | Cunningham ............... 600/587 |
| 6,124,597 | A | 9/2000 | Shehada et al. |
| 6,171,303 | B1 | 1/2001 | Ben-Haim et al. |
| 6,200,310 | B1 | 3/2001 | Ben-Haim et al. |
| 6,205,349 | B1 | 3/2001 | Kim et al. |
| 6,238,348 | B1 | 5/2001 | Crowley et al. |
| 6,277,082 | B1 | 8/2001 | Gambale |
| 6,368,284 | B1 | 4/2002 | Bardy |
| 6,406,420 | B1 | 6/2002 | McCarthy et al. |
| 6,564,088 | B1 | 5/2003 | Soller et al. |
| 6,604,000 | B2 | 8/2003 | Lu |
| 6,697,657 | B1 | 2/2004 | Shehada et al. |
| 6,827,690 | B2 | 12/2004 | Bardy |
| 6,937,899 | B2 | 8/2005 | Sheldon et al. |
| 7,039,462 | B2 | 5/2006 | Pastore et al. |
| 7,181,268 | B2 | 2/2007 | Sheldon et al. |
| 7,215,997 | B2 | 5/2007 | Yu et al. |
| 7,299,087 | B2 | 11/2007 | Bardy |
| 7,558,622 | B2 | 7/2009 | Tran |
| 7,577,478 | B1 | 8/2009 | Kroll et al. |
| 7,640,046 | B2 | 12/2009 | Pastore et al. |
| 2002/0045811 | A1 | 4/2002 | Kittrell et al. |
| 2002/0111551 | A1 | 8/2002 | Erlach et al. |
| 2003/0045805 | A1* | 3/2003 | Sheldon et al. ............... 600/513 |
| 2003/0055466 | A1 | 3/2003 | Ben-Haim et al. |
| 2003/0120151 | A1 | 6/2003 | Constantinides |
| 2003/0129750 | A1 | 7/2003 | Schwartz |
| 2003/0139667 | A1 | 7/2003 | Hewko et al. |
| 2004/0111016 | A1 | 6/2004 | Casscells et al. |
| 2005/0043675 | A1 | 2/2005 | Pastore et al. |
| 2005/0171414 | A1 | 8/2005 | Demos et al. |
| 2005/0283195 | A1 | 12/2005 | Pastore et al. |
| 2005/0288721 | A1 | 12/2005 | Girouard et al. |
| 2006/0009811 | A1 | 1/2006 | Sheldon et al. |
| 2006/0259087 | A1 | 11/2006 | Baynham et al. |
| 2006/0287684 | A1 | 12/2006 | Baynham et al. |
| 2007/0043393 | A1 | 2/2007 | Brockway et al. |
| 2007/0054871 | A1 | 3/2007 | Pastore et al. |
| 2007/0150005 | A1 | 6/2007 | Sih et al. |
| 2007/0150015 | A1 | 6/2007 | Zhang et al. |
| 2007/0162081 | A1 | 7/2007 | Yu et al. |
| 2007/0276453 | A1 | 11/2007 | Hill et al. |
| 2008/0058661 | A1 | 3/2008 | Bardy |
| 2008/0081354 | A1 | 4/2008 | Qu et al. |
| 2008/0091138 | A1 | 4/2008 | Pastore et al. |
| 2008/0177194 | A1 | 7/2008 | Zhang et al. |
| 2008/0287818 | A1 | 11/2008 | Shelchuk et al. |
| 2009/0082781 | A1 | 3/2009 | Tran et al. |
| 2009/0171228 | A1 | 7/2009 | Fischell et al. |

OTHER PUBLICATIONS

U.S. Appl. No. 10/871,865, Final Office Action mailed Dec. 31, 2007, 17 pgs.

U.S. Appl. No. 10/871,865, Non-Final Office Action mailed Jan. 22, 2007, 16 pgs.

U.S. Appl. No. 10/871,865, Non-Final Office Action mailed Feb. 5, 2009, 11 pgs.

U.S. Appl. No. 10/871,865, Non-Final Office Action mailed Feb. 23, 2006, 20 pgs.

U.S. Appl. No. 10/871,865, Non-Final Office Action mailed Jul. 9, 2007, 16 pgs.

U.S. Appl. No. 10/871,865, Non-Final Office Action mailed Aug. 7, 2008, 12 pgs.

U.S. Appl. No. 10/871,865, Non-Final Office Action mailed Aug. 25, 2006, 16 pgs.

U.S. Appl. No. 10/871,865, Notice of Allowance mailed Aug. 24, 2009, 6 Pgs.

U.S. Appl. No. 10/871,865, Response filed Jan. 12, 2006 to Restriction Requirement mailed Dec. 12, 2005, 24 pgs.

U.S. Appl. No. 10/871,865, Response filed Mar. 31, 2008 to Final Office Action mailed Dec. 31, 2007, 31 pgs.

U.S. Appl. No. 10/871,865, Response filed Apr. 23, 2007 to Non-Final Office Action mailed Jan. 22, 2007, 31 pgs.

U.S. Appl. No. 10/871,865, Response filed May 5, 2009 to Non-Final Office Action mailed Feb. 5, 2009, 14 pgs.

U.S. Appl. No. 10/871,865, Response filed Jun. 23, 2006 to Non-Final Office Action mailed Feb. 23, 2006, 34 pgs.

U.S. Appl. No. 10/871,865, Response filed Oct. 9, 2007 to Non-Final Office Action mailed Jul. 9, 2007, 31 pgs.

U.S. Appl. No. 10/871,865, Response filed Nov. 4, 2008 to Non-Final Office Action mailed Aug. 7, 2008, 28 pgs.

U.S. Appl. No. 10/871,865, Response filed Nov. 6, 2006 to Non-Final Office Action mailed Aug. 25, 2006, 32 pgs.

U.S. Appl. No. 10/871,865, Restriction Requirement mailed Dec. 12, 2005, 5 pgs.

* cited by examiner

METHOD AND APPARATUS FOR LOCALIZING MYOCARDIAL INFARCTION DURING CATHETERIZATION

CROSS REFERENCE TO RELATED APPLICATION

This application is a divisional of U.S. application Ser. No. 10/871,865, filed Jun. 18, 2004, now issued as U.S. Pat. No. 7,640,046, which is hereby incorporated by reference in its entirety.

FIELD OF THE INVENTION

This document generally relates to cardiac rhythm management systems and particularly, but not by way of limitation, to a system for localizing infarcted tissue in a heart having suffered myocardial infarction based on tissue properties that distinguish the infarcted tissue from normal myocardial tissue.

BACKGROUND

The heart is the center of a person's circulatory system. It includes an electro-mechanical system performing two major pumping functions. The heart includes four chambers: right atrium (RA), right ventricle (RV), left atrium (LA), and left ventricle (LV). The left portions of the heart, including LA and LV, draw oxygenated blood from the lungs and pump it to the organs of the body to provide the organs with their metabolic needs for oxygen. The right portions of the heart, including RA and RV, draw deoxygenated blood from the body organs and pump it to the lungs where the blood gets oxygenated. The efficiency of the pumping functions, indicative whether the heart is normal and healthy, is indicated by measures of hemodynamic performance, such as parameters related to intracardiac blood pressures and cardiac output.

In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue cause dyssynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply. The necrotic tissue, known as infarcted tissue, loses the contractile properties of the normal, healthy myocardial tissue. Consequently, the overall contractility of the myocardium is weakened, resulting in decreased cardiac output. As a physiological compensatory mechanism that acts to increase cardiac output in response to MI, the LV diastolic filling pressure increases as the pulmonary and venous blood volume increases. This increases the LV preload (stress on the LV wall before its contracts to eject blood). One consequence is the progressive change of the LV shape and size, a processes referred to as remodeling. Remodeling is initiated in response to a redistribution of cardiac stress and strain caused by the impairment of contractile function in the infarcted tissue as well as in nearby and/or interspersed viable myocardial tissue with lessened contractility due to the infarct. The remodeling starts with expansion of the region of the infarcted tissue and progresses to a chronic, global expansion in the size and change in the shape of the entire LV. Although the process is initiated by the compensatory mechanism that increases cardiac output, the remodeling ultimately leads to further deterioration and dysfunction of the myocardium. Consequently, post MI patients experience impaired hemodynamic performance and have a significantly increased risk of developing heart failure.

For effectively and/or efficiently applying surgical or any other treatments to control the remodeling process, there is a need for localizing the infarcted tissue in a heart having suffered MI.

SUMMARY

A catheter with a tissue property sensor provides for localization of myocardial infarction (MI) by utilizing one or more differences between properties of infarcted myocardial tissue and properties of normal myocardial tissue. The tissue property sensor is to be placed on a cardiac wall during catheterization to sense at least one tissue property allowing for detection of MI.

In one embodiment, a system for localizing MI includes a catheter, a myocardial tissue property sensor, and a tissue property analyzer. The catheter includes a distal end configured for placement in a location on the cardiac wall. The myocardial tissue property sensor is incorporated into the distal end of the catheter to be placed in a myocardial location to sense a signal indicative of at least one tissue property. The tissue property analyzer includes an input to receive the sensed signal and an output indicative of whether the sensed signal indicates infarcted tissue.

In one embodiment, the myocardial tissue property sensor includes a contractility sensor. The contractility sensor includes an accelerometer array with a plurality of accelerometers to sense acceleration signals related to displacement of the cardiac wall. The acceleration signals indicate a tissue property allowing for detection of infracted tissue.

In one embodiment, the tissue property analyzer includes a parameter generator and a comparator. The parameter generator produces a parameter based on the sensed signal. The comparator compares the parameter to a predetermined threshold and indicates a detection of infarcted tissue based on the comparison.

In one embodiment, the myocardial tissue property sensor is incorporated into the distal end of the catheter to be placed in a plurality of myocardial locations, one at a time, over a portion of the cardiac wall to sense signals each indicative of the tissue property for one of the myocardial locations. The tissue property analyzer includes a tissue property mapping module that produces a tissue property map presenting a measure of the tissue property over the portion of the cardiac wall based on the sensed signals.

In one embodiment, methods for localizing MI are provided. A sensor is placed in a myocardial location. A signal is sensed using to sensor to indicate at least one tissue property in the myocardial location. Infarcted tissue is detected based on the signal. In one embodiment, the signal is indicative of myocardial contractility and allows for detection of the infracted tissue.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

The drawings illustrate generally, by way of example, but not by way of limitation, various embodiments discussed in the present document. The drawing are for illustrative purposes only and not to scale nor anatomically accurate.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a method and system for localizing MI (i.e., identifying regions of infarcted tissue) based on myocardial tissue properties. After MI, various properties of the infarcted tissue change during the scar formation process. By sensing one or more tissue properties across a portion of the cardiac wall, infarcted regions are localized as areas where the one or more tissue properties are determined to be associated with infarcted tissue. The method and system are also useable for monitoring any effect of therapies delivered to control the post-MI remodeling process by treating the infarcted tissue.

Figure 1:
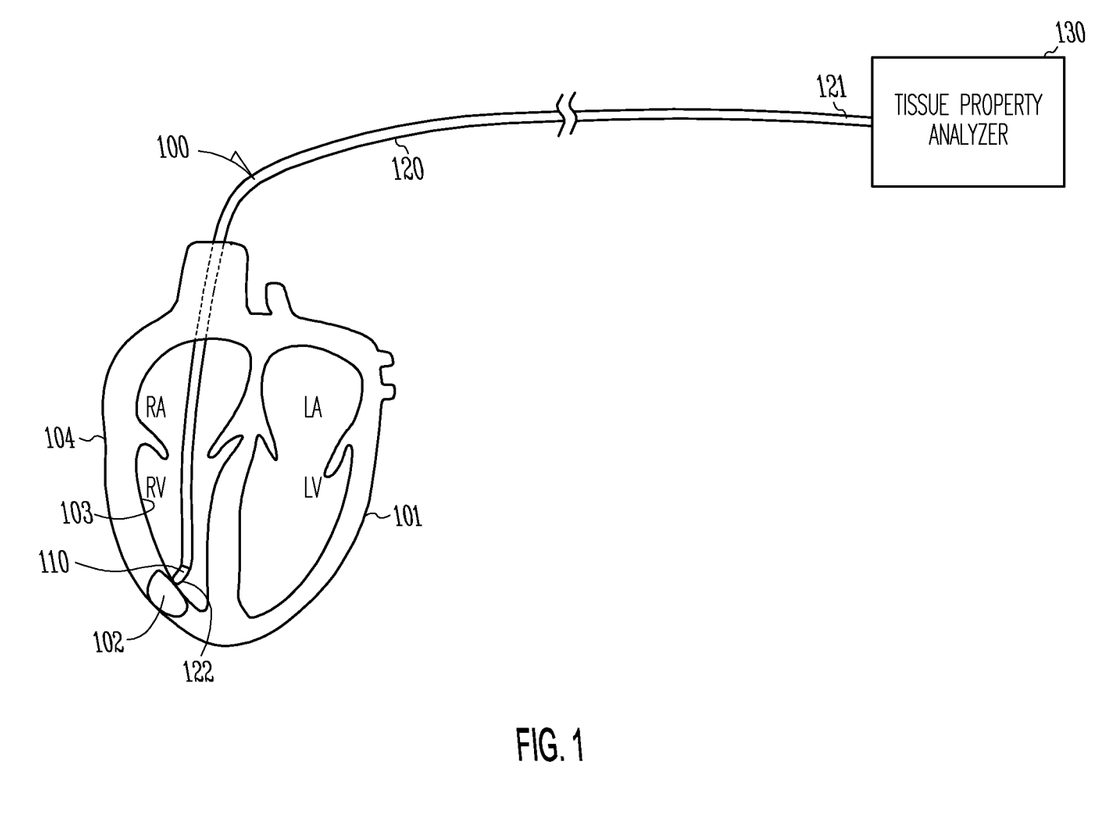
FIG. 1 is an illustration of one embodiment of a system providing for localization of MI during cardiac catheterization, in which the system is used for an endocardial application, and portions of an environment in which the system is used.
Figure 2:
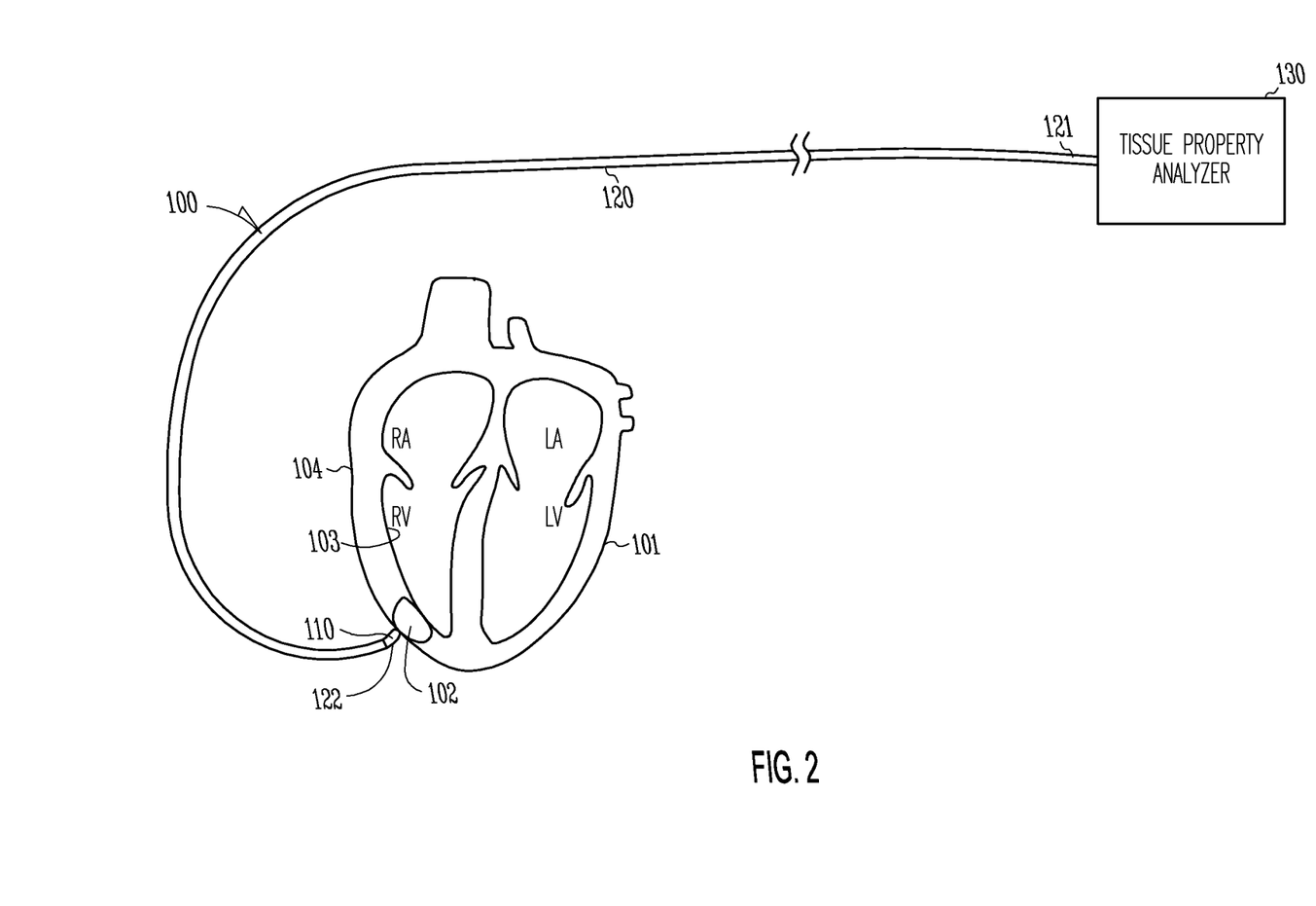
FIG. 2 is an illustration of another embodiment of the system providing for localization of MI during cardiac catheterization, in which the system is used for an epicardial application, and portions of an environment in which the system is used.

FIGS. 1 and 2 illustrate two embodiments of a system 100 providing for localization of MI and portions of an environment in which system 100 is used. System 100 includes a catheter 120 that provides for localization of at least one infarcted region 102 in a heart 101 that has suffered MI. Heart 101 includes an endocardial wall 103 and an epicardial wall 104. Catheter 120 has a proximal end 121 and a distal end 122. A myocardial tissue property sensor 110 is incorporated into catheter 120 at distal end 122. In the embodiment illustrated in FIG. 1, myocardial tissue property sensor 110 is configured for placement in various locations or regions on endocardial surface 103. In the embodiment illustrated in FIG. 2, myocardial tissue property sensor 110 is configured for placement in various locations or regions on epicardial surface 104. Myocardial tissue property sensor 110 senses one or more signals indicative of myocardial tissue properties. Proximal end 121 is outside the body and connected to an external tissue property analyzer 130. Tissue property analyzer 130 analyzes the one or more signals sensed by myocardial tissue property sensor 110 to detect infarcted tissue. Catheter 120 provides for electrical and/or other connections between myocardial tissue property sensor 110 and tissue property analyzer 130 to allow transmission of the one or more sensed signals.

Myocardial tissue property sensor 110 is configured for placement in a location or a region on endocardial wall 103 and/or epicardial wall 104. In one embodiment, at least a portion of myocardial tissue property sensor 110 is configured for penetration into the myocardial tissue in the location or region on the cardiac wall including endocardial wall 103 and/or epicardial wall 104. The penetration allows sensing of tissue properties that must be achieved with a sensor in the tissue and stabilization of the sensor in the location or region of the cardiac wall. Myocardial tissue property sensor 110, including all of its embodiments discussed below, includes at least a portion configured for tissue penetration when such a penetration is considered necessary and/or adequate. In all discussions related to sensor placement below, "in a location on a cardiac wall," "in a region on a cardiac wall," and like expressions include penetration of at least a portion of myocardial tissue property sensor 110 into tissue when such a penetration is considered necessary and/or adequate. Whether such a penetration is considered necessary and/or adequate depends on the need for reliable sensing of tissue property and/or the need for stabilizing the placement of myocardial tissue property sensor 110 during sensing, as understood by any person skilled in the art of cardiac catheterization and tissue property sensing.

In one embodiment, catheter 120 is a catheter dedicated to MI localization by myocardial tissue property sensing. In another embodiment, myocardial tissue property sensor 110 is incorporated into a catheter used for other diagnostic and/or therapeutic purposes. Examples of catheter 120 in this embodiment include, but are not limited to, a catheter for assessment of hemodynamic function, a catheter for mapping of cardiovascular structure, a substance (such as pharmaceutical and biological agents) delivery catheter, an ablation catheter, a pacing lead, and a defibrillation lead. In one embodiment, as illustrated in FIG. 1, catheter 120 is configured for transvenous or transarterial catheterization with distal end 122 reaching endocardial wall 103. In another embodiment, as illustrated in FIG. 2, catheter 120 is configured for intercostal catheterization with distal end 122 reaching epicardial wall 104. In one specific embodiment, the intercostal catheterization is performed using a minimally invasive surgical technique. For example, a small incision is made on chest between two ribs. Catheter 120 is inserted through the incision into intercostal space to reach heart 101 under guidance provided with some imaging technique. In one embodiment, catheter 120 is configured to be suitable for transvenous, transarterial, and intercostal catheterization.

For all descriptions below, the term "myocardial" includes "endocardial" and "epicardial," and the term "cardiac wall" includes "endocardial wall" and "epicardial wall." For example, any "myocardial tissue property sensor" is configured as an "endocardial tissue property sensor" for endocardial placement over a portion of the myocardium in one embodiment, as illustrated in FIG. 1, and an "epicardial tissue property sensor" for epicardial placement over a portion of the myocardium in another embodiment, as illustrated in FIG. 2. A "myocardial location" includes a location on endocardial wall 103 or epicardial wall 104 or locations in myocardial tissue accessible through endocardial wall 103 or epicardial wall 104.

Figure 3:
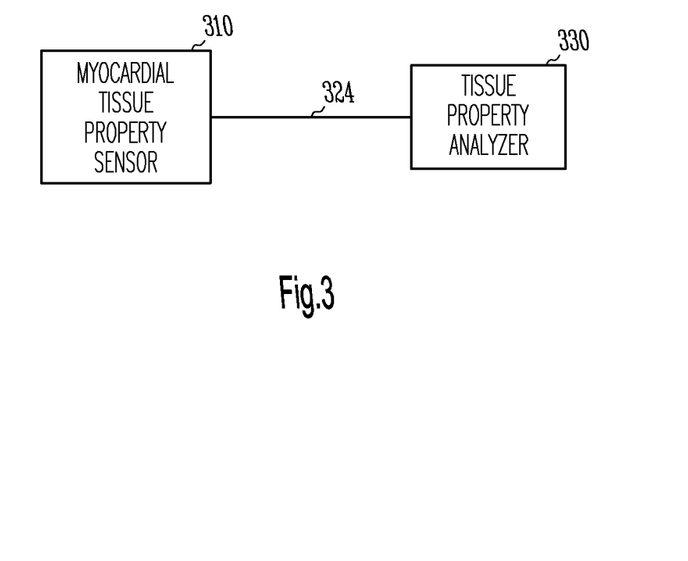
FIG. 3 is block diagram illustrating one embodiment of a circuit of the system providing for localization of MI during cardiac catheterization.

FIG. 3 illustrates one embodiment of a circuit of system 100. The circuit includes a myocardial tissue property sensor 310 and a tissue property analyzer 330. Myocardial tissue property sensor 310 represents one embodiment of myocardial tissue property sensor 110. Tissue property analyzer 330 represents one embodiment of tissue property analyzer 130. A sensor link 324, which couples myocardial tissue property sensor 310 and tissue property analyzer 330 via electrical and/or other connections, is included in catheter 120 and extends from proximal end 121 to distal end 122.

Myocardial tissue property sensor 310 includes a sensor that senses at least one signal indicative of a tissue property that changes as a result of MI. Examples of myocardial tissue property sensor 310 include, but are not limited to, an optical sensor, an acoustic sensor, a temperature sensor, a contractility sensor, and a drug response sensor. These examples are discussed below with reference to FIGS. 5, 7, 9, 11, and 13. Tissue property analyzer 330 includes an input coupled to myocardial tissue property sensor 220 through sensor link 324 and an output indicating detection of infarcted tissue. In one embodiment, tissue property analyzer 330 includes a parameter generator and an MI detector. The parameter generator produces at least one parameter representative of the tissue property indicated by the sensed signal. The MI detector includes a comparator with a signal input receiving the parameter, a threshold input receiving a predetermined threshold, and an output indicating a detection of the infarcted tissue based on a comparison between the signal and the threshold. In a specific embodiment, the threshold is determined based on a study evaluating a patient population. In another embodiment, tissue property analyzer 330 includes a tissue property mapping module to produce a tissue property map presenting a measure of at least one tissue property over at least a portion of the cardiac wall. In a further embodiment, tissue property analyzer 330 includes an MI detector to detect one or more infarcted regions based on the tissue property map.

Figure 4:
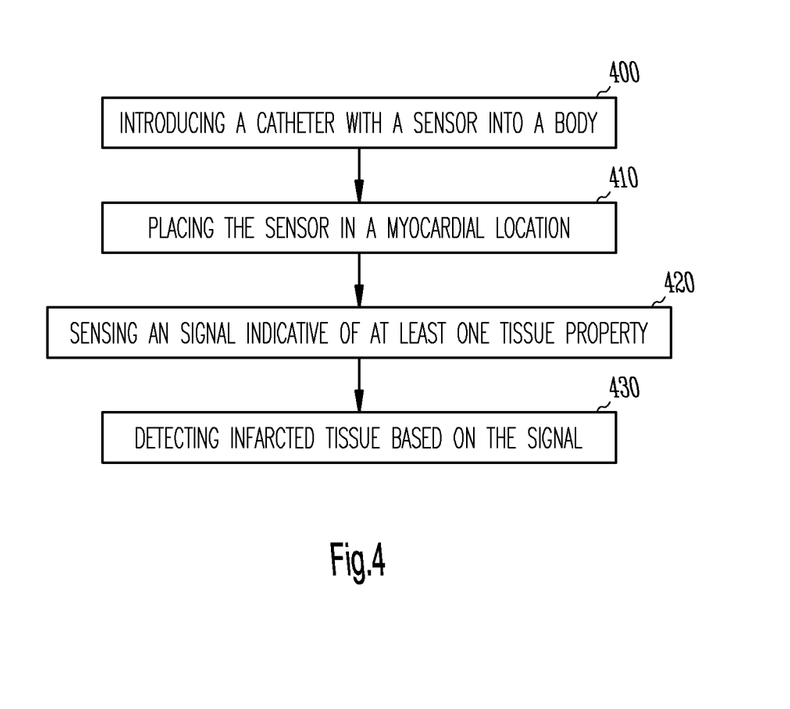
FIG. 4 is a flow chart illustrating one embodiment of a method for localizing MI during cardiac catheterization.

FIG. 4 is a flow chart illustrating one embodiment of a method for localizing MI during cardiac catheterization. In one specific embodiment, the method is performed with system 100 including the circuit of FIG. 3.

A catheter is introduced into a body to provide for access to the heart at 400. The catheter includes a sensor at its end portion. The sensor is placed in a location on the cardiac wall at 410. A signal indicative of at least one tissue property of the tissue in that myocardial location is sensed at 420. The tissue property indicated by the sensed signal is a tissue property that changes as a result of MI and provides for distinction between normal and infarcted tissues. Examples of the sensed signal include, but are not limited to an optical signal, an acoustic signal, a signal indicative of myocardial contractility, a temperature signal, and a signal indicative of a myocardial tissue response to a drug delivery. These examples are further discussed below with reference to FIGS. 6, 8, 10, 12, and 14. The infarcted tissue is detected based on the sensed signal at 430. The detection indicates that the tissue in the myocardial location where the sensor is placed is infarcted tissue.

In one embodiment, the sensor is moved to and placed in a plurality of myocardial locations, one at a time, within at least a portion of the cardiac wall to sense the signal at each of these locations. The signal sensed at each location indicates whether the tissue in that location is infarcted tissue. In one embodiment, a parameter representative of the tissue property for each location is produced and compared to a predetermined threshold value. Infarcted tissue is detected for each location based on an outcome of the comparison. In another embodiment, a tissue property map is produced to present a measure of the at least one tissue property over the at least the portion of the cardiac wall. Boundaries of one or more infarcted regions are identified based on the tissue property map.

Example 1

System with Optical Sensor

Figure 5:
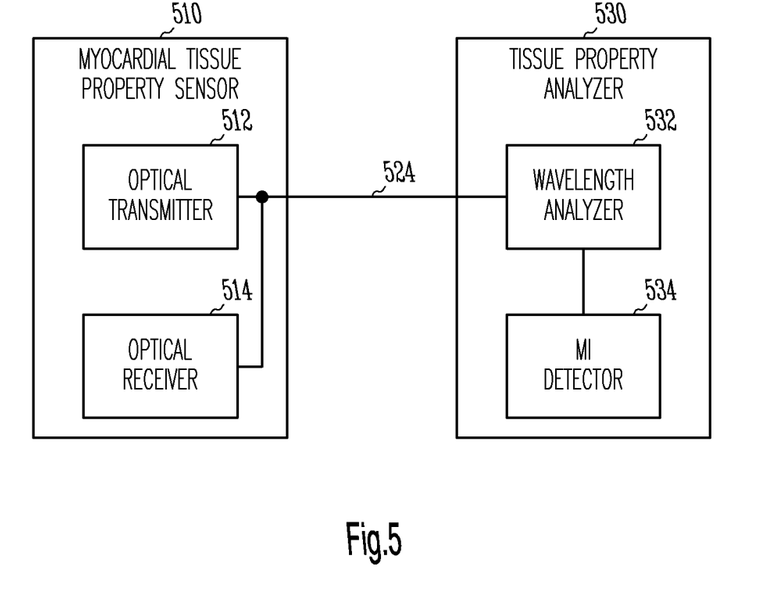
FIG. 5 is block diagram illustrating one specific embodiment of the circuit of the system providing for localization of MI in which an optical sensor is used.

FIG. 5 illustrates one specific embodiment of the circuit of system 100. The circuit provides for localization of MI using an optical sensor. This circuit includes a myocardial tissue property sensor 510, which is a specific embodiment of myocardial tissue property sensor 310, and a tissue property analyzer 530, which is a specific embodiment of tissue property analyzer 330. A sensor link 524, which is a specific embodiment of sensor link 324, couples myocardial tissue property sensor 510 and tissue property analyzer 530.

Myocardial tissue property sensor 510 is an optical sensor including an optical transmitter 512 and an optical receiver 514. Optical transmitter 512 emits a light into tissue in a myocardial location where myocardial tissue property sensor 510 is placed. The light includes a visible light, an infrared light, an ultraviolet light, or a combination of such lights.

Optical receiver 514 receives an optical signal related to the emitted light while the light is being emitted. The optical signal includes fluorescence generated from myocardial tissue in response to the emitted light. The fluorescence has an optical spectrum including wavelengths (colors) being a function of the tissue property. Thus, the fluorescence generated from infarcted tissue includes wavelengths that are different from the wavelengths of the fluorescence generated from normal tissue. In one embodiment, to increase the signal-to-noise ratio of the optical signal including the fluorescence, a fluorescent dye sensitive to transmembrane potentials is injected through catheter 120. In one specific embodiment, myocardial tissue property sensor 510 includes an injection device allowing the injection of the fluorescent dye. Catheter 120 includes a lumen allowing passage of the fluorescent dye through the catheter. In a further embodiment, to further increase the signal-to-noise ratio, subthreshold electrical stimuli, such as subthreshold pacing pulses, are delivered to the heart. The subthreshold electrical stimuli are electrical stimuli each having a stimulation amplitude that is below the threshold for myocardial tissue excitation. Myocardial tissue property sensor 510 includes at least one electrode allowing delivery of the electrical stimuli. In one specific embodiment, catheter 120 includes an electrical conductor allowing delivery of the electrical stimuli through the catheter.

Tissue property analyzer 530 includes a wavelength analyzer 532 and an MI detector 534. Wavelength analyzer 532 produces an optical spectrum of the optical signal received by optical receiver 514. MI detector 534 detects infarcted tissue based on the optical spectrum. In one embodiment, MI detector 534 detects the infarcted tissue when the optical spectrum differs from a template spectrum associated with normal tissue by a predetermined margin. In an alternative embodiment, MI detector 534 detects the infarcted tissue when the optical spectrum matches a template spectrum associated with known infarcted tissue within a predetermined margin. For example, NADH (the reduced form of Nicotinamide Adenine Dinucleotide) is a product of metabolism associated with myocardial ischemia. A template spectrum is thus obtained from an optical signal including fluorescence generated from tissue with elevated level of NADH. In these embodiments, the template spectrum and the predetermined margin are each determined based on a study evaluating a patient population. In another embodiment, MI detector 534 detects the infarcted tissue based on a substantial change in the optical spectrum when the optical sensor moves from one myocardial location to another myocardial location. A quantitative standard for the substantiality of the change is determined based on a study evaluating a patient population.

Figure 6:
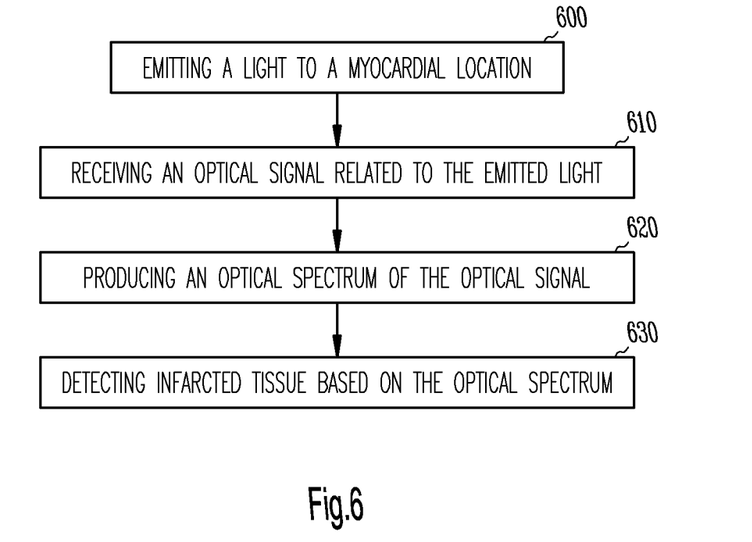
FIG. 6 is a flow chart illustrating one specific embodiment of the method for localizing MI in which an optical signal is sensed.

FIG. 6 is a flow chart illustrating one specific embodiment of the method for localizing MI. As a specific embodiment of steps 420 and 430 of FIG. 3, infarcted tissue is detected by sensing an optical signal.

A light is emitted to a myocardial location in a heart at 600. In one embodiment, a fluorescent dye sensitive to transmembrane potentials is also released to the myocardial location. In a further embodiment, electrical stimuli, such as pacing pulses, are delivered to the heart. An optical signal related to the emitted light is received at 610, while the light is being emitted. An optical spectrum of the received optical signal is produced at 620. Infarcted tissue is detected for the myocardial location based on the optical spectrum at 630. In one embodiment, the infarcted tissue is detected when the optical spectrum differs from a template spectrum associated with normal tissue by a predetermined margin. In an alternative embodiment, the infarcted tissue is detected when the optical spectrum matches a template spectrum associated with known infarcted tissue within a predetermined margin. In one embodiment, steps 600 through 620 are repeated for a plurality of myocardial locations. The infarcted tissue is detected based on the optical spectra produced all the myocardial locations. An infarcted tissue region includes one or more myocardial locations where the optical spectra for the adjacent myocardial locations are substantially different from the optical spectra for the one or more myocardial locations.

Example 2

System with Acoustic Sensor

Figure 7:
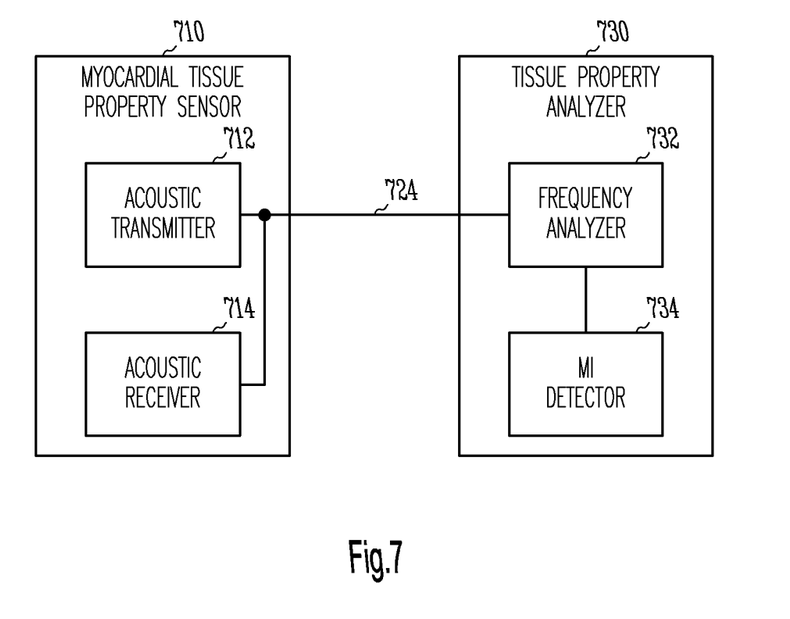
FIG. 7 is block diagram illustrating another specific embodiment of the circuit of the system providing for localization of MI in which an acoustic sensor is used.

FIG. 7 illustrates another specific embodiment of the circuit of system 100. The circuit provides for localization of MI using an acoustic sensor. This circuit includes a myocardial tissue property sensor 710, which is another specific embodiment of myocardial tissue property sensor 310, and a tissue property analyzer 730, which is another specific embodiment of tissue property analyzer 330. A sensor link 724, which is another specific embodiment of sensor link 324, couples myocardial tissue property sensor 710 and tissue property analyzer 730.

Myocardial tissue property sensor 710 is an acoustic sensor including an acoustic transmitter 712 and an acoustic receiver 714. Acoustic transmitter 712 emits an acoustic energy into tissue in a myocardial location where myocardial tissue property sensor 710 is placed. In one embodiment, acoustic transmitter 712 includes a speaker to transmit an audible sound pulse. In another embodiment, acoustic transmitter 712 includes an ultrasound transmitter to transmit an ultrasound pulse. In one embodiment, acoustic transmitter 712 includes a piezoelectric crystal. Acoustic receiver 714 receives an acoustic signal related to the emitted acoustic energy. The acoustic signal includes echoes of the audible sound pulse or the ultrasound pulse. As a result of the scar formation process, infarcted tissue is stiffer than normal tissue. The echoes from infarcted tissue have a pitch distinguishable from the pitch associated of normal tissue.

Tissue property analyzer 730 includes a frequency analyzer 732 and an MI detector 734. Frequency analyzer 732 produces an acoustic spectrum of the received acoustic signal. MI detector 734 detects infarcted tissue based on the acoustic spectrum. In one embodiment, MI detector 734 detects the infarcted tissue when the acoustic spectrum differs from a template spectrum associated with normal tissue by a predetermined margin. In an alternative embodiment, MI detector 534 detects the infarcted tissue when the acoustic spectrum matches a template spectrum associated with known infarcted tissue within a predetermined margin. In these embodiments, the template spectrum and the predetermined margin are each determined based on a study evaluating a patient population. In another embodiment, MI detector 734 detects the infarcted tissue based on a substantial change in the acoustic spectrum when the acoustic sensor moves from one myocardial location to another myocardial location. A quantitative standard for the substantiality of the change is determined based on a study evaluating a patient population.

Figure 8:
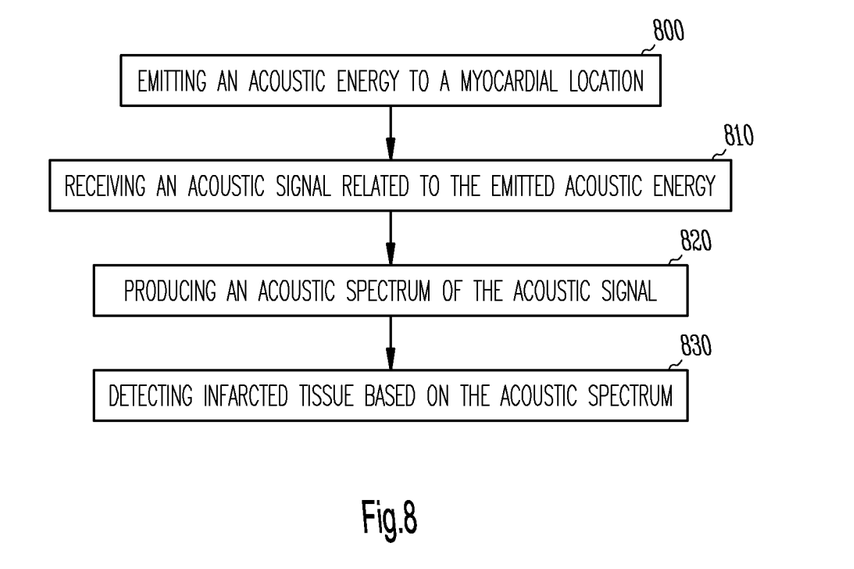
FIG. 8 is a flow chart illustrating another specific embodiment of the method for localizing MI in which an acoustic signal is sensed.

FIG. 8 is a flow chart illustrating another specific embodiment of the method for localizing MI. As another specific embodiment of steps 420 and 430 of FIG. 3, infarcted tissue is detected by sensing an acoustic signal.

An acoustic energy is emitted to a myocardial location at 800. In one embodiment, the acoustic energy is in a form of an audible sound. In another embodiment, the acoustic energy is in a form of an ultrasound. An acoustic signal related to the emitted acoustic energy is received at 810. The acoustic signal includes echoes of the audible sound or ultrasound. An acoustic spectrum of the received acoustic signal is produced at 820. Infarcted tissue is detected based on the acoustic spectrum at 830. In one embodiment, the infarcted tissue is detected when the acoustic spectrum differs from a template spectrum associated with normal tissue by a predetermined margin. In an alternative embodiment, the infarcted tissue is detected when the acoustic spectrum matches a template spectrum associated with known infarcted tissue within a predetermined margin. In another embodiment, steps 800 through 820 are repeated for a plurality of myocardial locations. The infarcted tissue is detected based on the acoustic spectra produced for the plurality of myocardial locations. An infarcted tissue region includes one or more myocardial locations where the acoustic spectra for the adjacent myocardial locations are substantially different from the acoustic spectra for the one or more myocardial locations.

Example 3

System with Contractility Sensor

Figure 9:
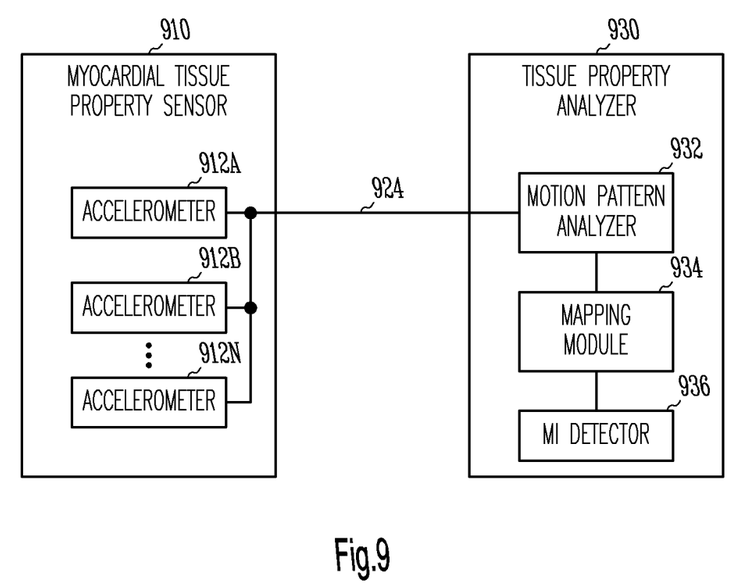
FIG. 9 is block diagram illustrating another specific embodiment of the circuit of the system providing for localization of MI in which a contractility sensor is used.

FIG. 9 illustrates another specific embodiment of the circuit of system 100. The circuit provides for localization of MI using a contractility sensor. This circuit includes a myocardial tissue property sensor 910, which is another specific embodiment of myocardial tissue property sensor 310, and a tissue property analyzer 930, which is another specific embodiment of tissue property analyzer 330. A sensor link 924, which is another specific embodiment of sensor link 324, couples myocardial tissue property sensor 910 and tissue property analyzer 930.

Myocardial tissue property sensor 910 is a contractility sensor that senses one or more signals indicative of myocardial contractility in a myocardial region. In one embodiment, the contractility sensor includes an accelerometer array including a plurality of accelerometers 912A, 912B, . . . , and 912N to sense acceleration signals from a plurality of locations constituting the myocardial region.

Tissue property analyzer 930 includes a motion pattern analyzer 932, a mapping module 934, and an MI detector 936. Motion pattern analyzer 932 produces a cardiac wall motion pattern for the myocardial region based on the sensed one or more signals indicative of myocardial contractility in the myocardial region. Mapping module 932 produces a contractility map presenting cardiac wall motion patterns for a plurality of myocardial regions within at least a portion of a cardiac wall. MI detector 936 detects infarcted tissue based on the contractility map. Infarcted tissue regions are detected by identifying dyskinetic and/or hypokinetic regions on the contractility map.

Figure 10:
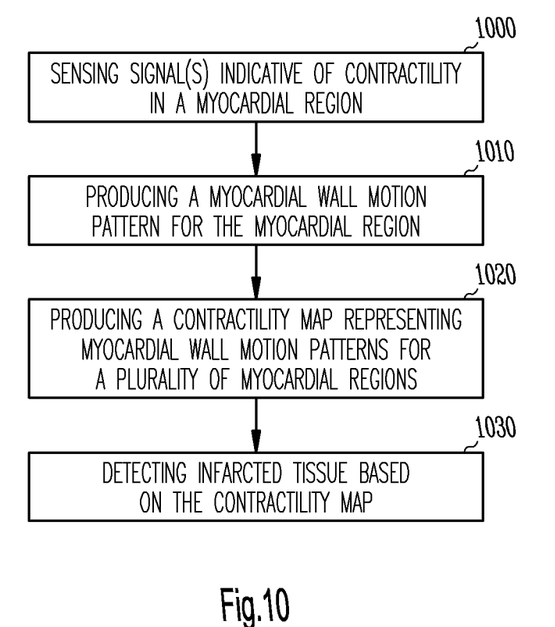
FIG. 10 is a flow chart illustrating another specific embodiment of the method for localizing MI in which a signal indicative of a myocardial contractility is sensed.

FIG. 10 is a flow chart illustrating another specific embodiment of the method for localizing MI. As another specific embodiment of steps 420 and 430 of FIG. 3, infarcted tissue is detected by sensing a signal indicative of a myocardial contractility.

One or more signals indicative of myocardial contractility in a myocardial region is sensed at 1000. In one embodiment, this includes sensing a plurality of acceleration signals from the myocardial region. A cardiac wall motion pattern for the myocardial region is produced based on the sensed one or more signals at 1010. Steps 1000 and 1010 are repeated for a plurality of myocardial regions, and a contractility map presenting cardiac wall motion patterns for the plurality of myocardial regions is produced at 1020. Infarcted tissue is detected based on the contractility map at 1030. In one embodiment, the infarcted tissue is detected by identifying dyskinetic and/or hypokinetic regions on the contractility map. In one embodiment, infarcted tissue is detected by identifying myocardial regions associated with cardiac wall displacements that are substantially smaller than the cardiac wall displacements of other myocardial regions.

Example 4

System with Temperature Sensor

Figure 11:
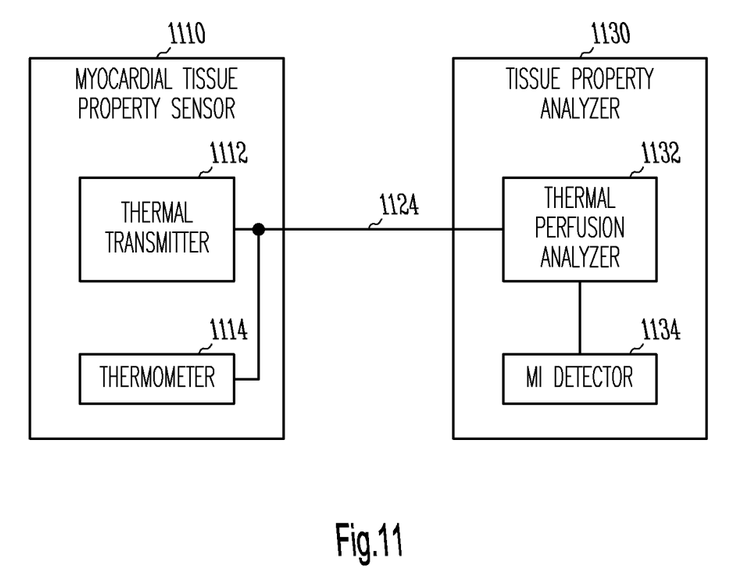
FIG. 11 is block diagram illustrating another specific embodiment of the circuit of the system providing for localization of MI in which a temperature sensor is used.

FIG. 11 illustrates one specific embodiment of the circuit of system 100. The circuit provides for localization of MI using a temperature sensor. This circuit includes a myocardial tissue property sensor 1110, which is another specific embodiment of myocardial tissue property sensor 310, and a tissue property analyzer 1130, which is another specific embodiment of tissue property analyzer 330. A sensor link 1124, which is another specific embodiment of sensor link 324, couples myocardial tissue property sensor 1110 and tissue property analyzer 1130.

Myocardial tissue property sensor 1110 is a temperature sensor including a thermal transmitter 1112 and a thermometer 1114. Thermal transmitter 1112 emits a thermal energy into tissue in a myocardial location where myocardial tissue property sensor 1110 is placed. In one embodiment, the thermal energy raises the temperature at the myocardial location. In another embodiment, the thermal energy lowers the temperature at the cardiac wall location. In one embodiment, myocardial tissue property sensor 1110 includes an injection device allowing injection of a thermal dilution liquid. In one specific embodiment, catheter 120 includes a lumen allowing passage of thermal dilution liquid. Thermometer 1114 senses a temperature related to the emitted thermal energy.

Tissue property analyzer 1130 includes a thermal perfusion analyzer 1132 and an MI detector 1134. Thermal perfusion analyzer 1132 produces a rate of temperature change (or thermal perfusion rate) being a change in the sensed temperature over a predetermined period of time. Infarcted tissue includes tissue properties related to thermal perfusion that are distinguishable from those of normal tissue. MI detector 1134 detects infarcted tissue based on the rate of temperature change. In one embodiment, MI detector 1134 detects the infarcted tissue when the rate of temperature change differs from a template rate associated with normal tissue by a predetermined margin. In an alternative embodiment, MI detector 1134 detects the infarcted tissue when the rate of temperature change matches a template spectrum associated with known infarcted tissue within a predetermined margin. In these embodiments, the template rate and the predetermined margin are each determined based on a study evaluating a patient population. In another embodiment, MI detector 1134 detects the infarcted tissue based on a substantial change in the rate of temperature change when the acoustic sensor moves from one myocardial location to another myocardial location. A quantitative standard for the substantiality of the change is determined based on a study evaluating a patient population.

Figure 12:
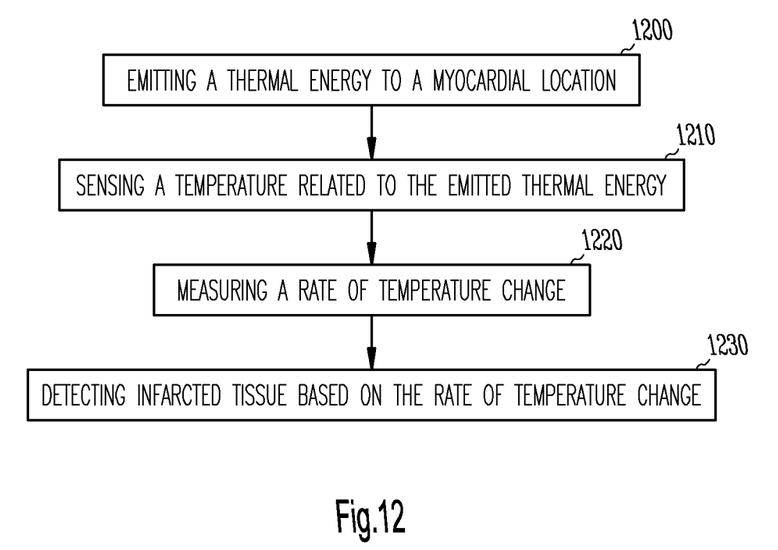
FIG. 12 is a flow chart illustrating another specific embodiment of the method for localizing MI in which a signal indicative of temperature is sensed.

FIG. 12 is a flow chart illustrating another specific embodiment of the method for localizing MI. As another specific embodiment of steps 420 and 430 of FIG. 3, infarcted tissue is detected by sensing a signal indicative of temperature.

A thermal energy is emitted to a myocardial location at 1200. In one embodiment, the thermal energy is emitted to heat the tissue in the myocardial location. In another embodiment, the thermal energy is emitted to cool the tissue in the myocardial location. In one embodiment, a thermal dilution liquid is released to the myocardial location. A temperature related to the emitted thermal energy is sensed at 1210, following the emission of the thermal energy. A rate of temperature change, or thermal perfusion rate, which is a change in the sensed temperature over a predetermined period of time, is measured for the myocardial location at 1220. Infarcted tissue is detected based on the rate of temperature change at 1230. In one embodiment, the infarcted tissue is detected when the rate of temperature change differs from a template rate associated with normal tissue by a predetermined margin. In an alternative embodiment, the infarcted tissue is detected when the rate of temperature change matches a template rate associated with known infarcted tissue within a predetermined margin. In another embodiment, steps 1200 through 1220 are repeated for a plurality of myocardial locations. The infarcted tissue is detected based on the rates of temperature change measured for the plurality of myocardial locations. An infarcted tissue region includes one or more myocardial locations where the rates of temperature change for the adjacent myocardial locations are substantially different from the rates of temperature change for the one or more myocardial locations.

Example 5

System with Drug Response Sensor

Figure 13:
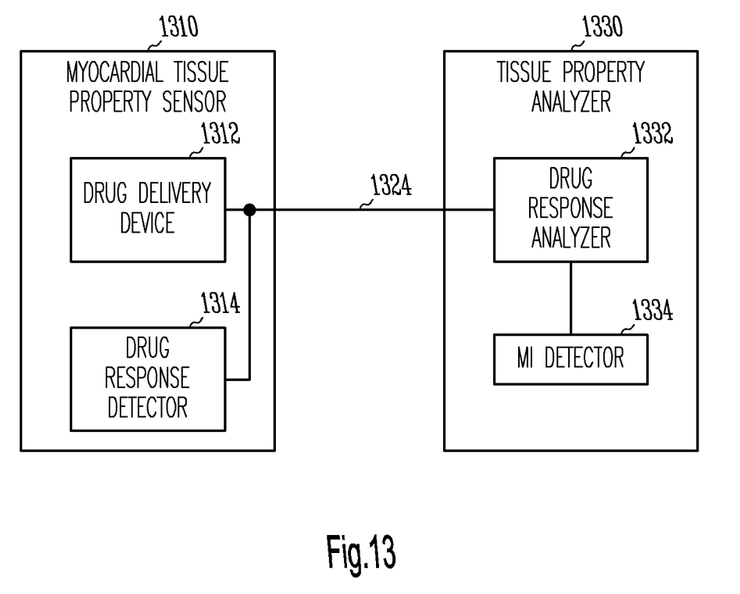
FIG. 13 is block diagram illustrating another specific embodiment of the circuit of the system providing for localization of MI in which a drug response sensor is used.

FIG. 13 illustrates another specific embodiment of the circuit of system 100. The circuit provides for localization of MI using a drug response sensor. This circuit includes a myocardial tissue property sensor 1310, which is another specific embodiment of myocardial tissue property sensor 310, and a tissue property analyzer 1330, which is another specific embodiment of tissue property analyzer 330. A sensor link 1324, which is another specific embodiment of sensor link 324, couples myocardial tissue property sensor 1310 and tissue property analyzer 1330.

Myocardial tissue property sensor 1310 is a drug response sensor including a drug delivery device 1312 and a drug response detector 1314. Drug delivery device 1312 releases a drug from a myocardial location where myocardial tissue property sensor 1310 is placed. The drug is of a type that causes a reaction from infarcted tissue that is distinguishable form a reaction from normal tissue. Examples of the drug include, but are not limited to, isoproterenol, dobutamine, nitroglycerin, and brain natriuretic peptide (BNP). In one embodiment, catheter 120 includes a lumen allowing passage of the drug from proximal end 121 to drug delivery device 1312. Drug response detector 1314 detects a signal indicative of a tissue response the delivered drug.

Tissue property analyzer 1330 includes a drug response analyzer 1332 and an MI detector 1334. Drug response analyzer 1332 produces a tissue response parameter as a tissue response parameter to the delivered drug based on the signal detected by drug response detector 1314. MI detector 1334 detects infarcted tissue based on the tissue response parameter to the delivered drug. In one embodiment, MI detector 1334 detects the infarcted tissue when the tissue response parameter differs from a template tissue response parameter associated with normal tissue by a predetermined margin. In an alternative embodiment, MI detector 1334 detects the infarcted tissue when the tissue response parameter matches a template tissue response parameter associated with known infarcted tissue within a predetermined margin. In these embodiments, the template tissue response parameter and the predetermined margin are each determined based on a study evaluating a patient population. In another embodiment, MI detector 1334 detects the infarcted tissue based on a substantial change in the tissue response parameter when the acoustic sensor moves from one myocardial location to another myocardial location. A quantitative standard for the substantiality of the change is determined based on a study evaluating a patient population.

In one specific embodiment, the drug includes an agent changing the contractility of myocardial tissue, such as isoproterenol. Drug response detector 1314 includes a contractility sensor to sense a signal indicative of myocardial contractility, such as an accelerometer. Drug response analyzer 1332 produces a parameter indicative of the myocardial contractility. In one embodiment, drug response analyzer 1332 includes a displacement analyzer to produce a parameter indicative of a cardiac wall displacement based on the acceleration signal sensed by the accelerometer. MI detector 1334 detects infarcted tissue based on the myocardial contractility, such as indicated by the parameter indicative of the cardiac wall displacement.

In another specific embodiment, the drug includes an agent known to produce a rapid, even perfusion in tissue, such as nitroglycerin. Drug response detector 1314 includes a drug concentration sensor. Drug response analyzer 1332 includes a drug perfusion analyzer that produces a rate of drug perfusion, which is a change in the sensed drug concentration over a predetermined period of time. MI detector 1334 detects the infarcted tissue based on the rate of drug perfusion.

Figure 14:
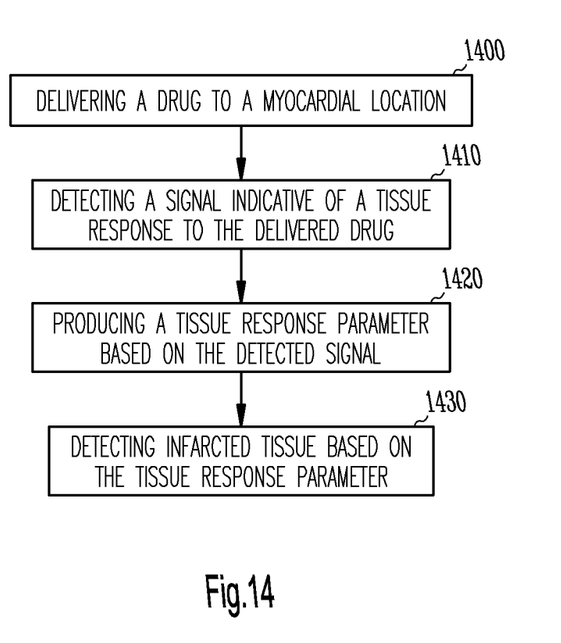
FIG. 14 is a flow chart illustrating another specific embodiment of the method for localizing MI in which a signal indicative of a myocardial tissue response to a drug delivery is sensed.

FIG. 14 is a flow chart illustrating another specific embodiment of the method for localizing MI. As another specific embodiment of steps 420 and 430 of FIG. 3, infarcted tissue is detected by sensing a signal indicative of a myocardial tissue response to a drug delivery.

A drug is delivered to a myocardial location at 1400. The drug provides for detection of infarcted tissue by examining a tissue property that is sensitive to the drug. Examples of the drug include, but are not limited to, isoproterenol, dobutamine, nitroglycerin, and BNP. A signal indicative of a tissue response to the delivered drug is detected at 1410. A tissue response parameter is produced based on the signal indicative of the tissue response at 1420. Infarcted tissue is detected for the myocardial region based on the tissue response parameter at 1430. In one embodiment, the infarcted tissue is detected when the tissue response parameter differs from a template tissue response parameter associated with normal tissue by a predetermined margin. In an alternative embodiment, the infarcted tissue is detected when the tissue response parameter matches a template tissue response parameter associated with known infarcted tissue within a predetermined margin. In another embodiment, steps 1400 and 1510 are repeated for a plurality of myocardial locations. The infarcted tissue is detected based on the tissue response parameters detected for the plurality of myocardial locations. An infarcted tissue region includes one or more myocardial locations where the tissue response parameters detected from the adjacent myocardial locations are substantially different from the tissue response parameters detected from the one or more myocardial locations.

In one specific embodiment, the drug includes an agent changing the contractility of myocardial tissue, such as nitroglycerin. The tissue response is indicated by a signal indicative of myocardial contractility, such as an acceleration sensed from the cardiac wall. Infarcted tissue is generally less sensitive to the agent than normal tissue. That is, the agent causes a smaller change in contractility in infarcted tissue than in normal tissue. The infarcted tissue is detected based on the signal indicative of myocardial contractility.

In another specific embodiment, the drug includes an agent known to perfuse rapidly and evenly in tissue, such as nitroglycerin. A drug concentration is sensed following the delivery of the drug. A rate of drug perfusion, which is a change in the sensed drug concentration over a predetermined period of time, is measured. Infarcted tissue is generally more resistant to the perfusion of the agent than normal tissue. The infarcted tissue is detected based on the rate of drug perfusion.

In General

It is to be understood that the above detailed description, including Examples 1 through 5, is intended to be illustrative, and not restrictive. For example, myocardial tissue property sensor 110 includes any sensor or sensors capable of sensing a signal indicative of a myocardial tissue property that changes as a result of MI. Tissue property analyzer 130 detects infarcted tissue generally by analyzing that signal. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A system for localizing myocardial infarction (MI) in a heart having a cardiac wall, the system comprising:
    a catheter including a distal end configured for placement in a location on the cardiac wall;
    a myocardial tissue property sensor incorporated into the distal end of the catheter and adapted to be placed in a myocardial region, the myocardial tissue property sensor including at least a portion configured to penetrate into tissue in the myocardial region and a contractility sensor being an accelerometer array including a plurality of accelerometers configured to sense acceleration signals from a plurality of myocardial locations in the myocardial region, the acceleration signals each indicative of a tissue property; and
    a tissue property analyzer including an input to receive the acceleration signals and an output indicative of whether the acceleration signals indicate infarcted tissue.

2. The system of claim 1, wherein the tissue property analyzer comprises a motion pattern analyzer to produce a cardiac wall motion pattern for the myocardial region based on the sensed acceleration signals.

3. The system of claim 2, wherein the contractility sensor is adapted to be placed in a plurality of myocardial regions, one at a time, over at least a portion of a cardiac wall, and wherein the tissue property analyzer further comprises a mapping module to produce a contractility map presenting cardiac wall motion patterns for the at least the portion of the cardiac wall.

4. The system of claim 3, wherein the tissue property analyzer further comprises an MI detector adapted to detect the infarcted tissue based on the contractility map.

5. The system of claim 4, wherein the MI detector is adapted to detect the infarcted tissue by identifying dyskinetic regions on the contractility map.

6. The system of claim 4, wherein the MI detector is adapted to detect the infarcted tissue by identifying hypokinetic regions on the contractility map.

7. The system of claim 1, wherein the tissue property analyzer comprises:
    a parameter generator to produce a parameter based on the acceleration signals; and
    a comparator including a signal input receiving the parameter, a threshold input receiving a predetermined threshold, and an output indicating a detection of infarcted tissue based on a comparison between the parameter and the threshold.

8. The system of claim 1, Therein the distal end of the catheter is configured for endocardial placement.

9. The system of claim 1, wherein the distal end of the catheter is configured for epicardial placement.

10. A method for localizing myocardial infarction (MI) in a heart having a cardiac wall, the method comprising:
    placing a myocardial tissue property sensor in a myocardial region on the cardiac wall, the myocardial tissue property sensor including at least a portion configured to penetrate into tissue in the myocardial region and an accelerometer array including a plurality of accelerometers;
    sensing a plurality of acceleration signals indicative of myocardial contractility from a plurality of myocardial locations in the myocardial region using the accelerometer array; and
    detecting infarcted tissue on the cardiac wall based on the plurality of acceleration signals.

11. The method of claim 10, wherein detecting the infarcted tissue comprises producing a cardiac wall motion pattern for the myocardial region based on the plurality of acceleration signals.

12. The method of claim 10, wherein detecting the infarcted tissue further comprises:
    producing a contractility map representing cardiac wall motion patterns for a plurality of myocardial regions; and
    detecting the infarcted tissue based on the contractility map.

13. The method of claim 12, wherein detecting the infarcted tissue based on the contractility map comprises identifying dyskinetic or hypokinetic regions on the contractility map.

14. The method of claim 13, wherein detecting the infarcted tissue based on the contractility map comprises identifying one or more regions of the plurality of myocardial regions associated with cardiac wall displacements that are substantially smaller than cardiac wall displacements of other regions of the plurality of myocardial regions.

15. The method of claim 10, wherein placing the accelerometer array on the cardiac wall comprises introducing a catheter into a body having the heart, and the accelerometer array is incorporated into a distal end of the catheter.

16. A system for localizing myocardial infarction (MI), the system comprising:
    a catheter including a distal end configured for myocardial placement;
    a myocardial contractility sensor adapted to sense signals indicative of myocardial contractility from myocardial locations constituting a myocardial region and including at least a portion configured to penetrate into tissue in the myocardial region, the myocardial contractility sensor incorporated into the distal end of the catheter and adapted to be placed in a plurality of the myocardial regions, one at a time, over at least a portion of a cardiac wall, the myocardial contractility sensor configured to sense signals each indicative of the myocardial contractility for one of the plurality of myocardial locations in one of the plurality of myocardial regions;
    a tissue property analyzer receiving the sensed signals, the tissue property analyzer including a tissue property mapping module adapted to produce a contractility map presenting a measure of the myocardial contractility over the at least the portion of the cardiac wall based on the sensed signals.

17. The system of claim 16, wherein the myocardial contractility sensor comprises a plurality of accelerometers.

18. The system of claim 17, wherein the distal end of the catheter is configured for endocardial placement.

19. The system of claim 17, wherein the distal end of the catheter is configured for epicardial placement.

20. The system of claim 17, wherein the tissue property analyzer further comprises a myocardial infarction detector to detect one or more infarcted regions based on the contractility map.

* * * * *